US011413197B2

(12) United States Patent
Houben et al.

(10) Patent No.: US 11,413,197 B2
(45) Date of Patent: Aug. 16, 2022

(54) ABSORBENT ARTICLES HAVING AN ANISOTROPIC FOAM ACQUISITION LAYER

(71) Applicants: ONTEX BV, Buggenhout (BE); ONTEX GROUP NV, Erembodegem (BE)

(72) Inventors: Annemie Houben, Ghent (BE); Miguel Angel Rodríguez Pérez, Valladolid (ES); Alberto López Gil, Valladolid (ES); Josias Tirado Mediavilla, Palencia (ES); Javier García González, Valladolid (ES); Lieven Dhooge, Ertvelde (BE); Ainas Weber, Bad Neuenahr-Ahrweiler (DE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 0 days.

(21) Appl. No.: 17/440,339

(22) PCT Filed: Mar. 17, 2020

(86) PCT No.: PCT/EP2020/057358
§ 371 (c)(1),
(2) Date: Sep. 17, 2021

(87) PCT Pub. No.: WO2020/187951
PCT Pub. Date: Sep. 24, 2020

(65) Prior Publication Data
US 2022/0142829 A1    May 12, 2022

(30) Foreign Application Priority Data
Mar. 18, 2019  (EP) .................................... 19163535

(51) Int. Cl.
*A61F 13/532*    (2006.01)
*A61F 13/15*    (2006.01)

(52) U.S. Cl.
CPC ...... *A61F 13/532* (2013.01); *A61F 13/15658* (2013.01)

(58) Field of Classification Search
CPC .............. A61F 13/15203; A61F 13/532; A61F 13/534; A61F 2013/15406;
(Continued)

(56) References Cited

U.S. PATENT DOCUMENTS 4,053,341 A * 10/1977 Kleiner ................... B32B 27/18
428/218
5,260,345 A * 11/1993 DesMarais ........ A61F 13/49012
521/905
(Continued)

FOREIGN PATENT DOCUMENTS

EP    1533586 A1    5/2005
EP    3456302 A1    3/2019
(Continued)

OTHER PUBLICATIONS

Ashida, K. et al., "Isocyanate-Based Foams," In: Landrock, A. H. (Ed.), Handbook of Plastic Foams (New Jersey, Noyes Publications) pp. 13-139 (1995).
(Continued)

*Primary Examiner* — Michele M Kidwell
(74) *Attorney, Agent, or Firm* — Vivicar Law, PLLC (57) ABSTRACT

The present invention relates to acquisition layers for use in absorbent articles, preferably of the disposable personal hygiene type. It discloses absorbent articles (7) comprising a liquid permeable topsheet (8), a liquid impermeable backsheet (9), an absorbent core (1) between the topsheet (8) and the backsheet (9) and an acquisition layer (2) between the
(Continued)

topsheet (8) and the absorbent core (1), said acquisition layer (2) having a width (w) and a length (l) along an acquisition plane and a thickness (t) extending perpendicular thereto. The absorbent core (1) comprises at least one absorbent material selected from the group consisting of fibrous absorbent materials and highly absorbent polymers. The acquisition layer (2) comprises a polymeric foam having an open cell and interconnected porous structure comprising an anisotropic cell structure having an axis of anisotropy (4) extending substantially parallel to a longest length of a plurality of substantially neighbouring cells (6), which is substantially perpendicular to the acquisition plane.

22 Claims, 5 Drawing Sheets

(58) Field of Classification Search
CPC .. A61F 2013/15463; A61F 2013/53081; A61F 2013/530817; A61F 2013/53908; A61F 2013/530868; A61F 2013/530802; A61F 13/5116; A61F 13/537; A61L 15/425
See application file for complete search history.

(56) References Cited

U.S. PATENT DOCUMENTS

| | | | |
|---|---|---|---|
| 5,817,704 A | 10/1998 | Shiveley et al. | |
| 5,856,366 A | 1/1999 | Shiveley et al. | |
| 5,869,171 A | 2/1999 | Shiveley et al. | |
| 6,207,724 B1 | 3/2001 | Hird et al. | |
| 6,852,905 B2 | 2/2005 | Baker | |
| 11,007,094 B2 * | 5/2021 | Houben | A61F 13/534 |
| 2002/0026977 A1 * | 3/2002 | Mason | B29C 44/24 |
| | | | 156/244.11 |
| 2002/0128338 A1 | 9/2002 | Hird et al. | |
| 2005/0192365 A1 | 9/2005 | Strandburg et al. | |
| 2007/0282025 A1 * | 12/2007 | Collier | C08F 2/32 |
| | | | 521/64 |
| 2013/0116646 A1 * | 5/2013 | Robles | A61F 13/534 |
| | | | 604/378 |
| 2014/0336606 A1 * | 11/2014 | Bewick-Sonntag | |
| | | | A61F 13/538 |
| | | | 604/378 |
| 2015/0065981 A1 * | 3/2015 | Roe | A61F 13/53717 |
| | | | 604/378 |
| 2015/0080823 A1 | 3/2015 | Thompson et al. | |
| 2015/0313763 A1 | 11/2015 | Bagger-Sjöbäck et al. | |
| 2015/0328060 A1 | 11/2015 | Bagger-Sjöbäck et al. | |
| 2015/0328061 A1 | 11/2015 | Bagger-Sjöbäck | |
| 2017/0119596 A1 * | 5/2017 | Bewick-Sonntag | |
| | | | A61F 13/15203 |
| 2018/0215890 A1 * | 8/2018 | Vo | C08J 9/142 |

FOREIGN PATENT DOCUMENTS

| | | | | |
|---|---|---|---|---|
| WO | 2008/008875 | * | 1/2008 | B32B 5/18 |
| WO | 2016200301 A1 | | 12/2016 | |
| WO | 2018122117 A1 | | 7/2018 | |
| WO | 2018167146 A1 | | 9/2018 | |

OTHER PUBLICATIONS

Gibson, L.J., et al., "The design of sandwich panels with foam cores," In: Cellular Solids, 2nd ed., Cambridge University Press, pp. 345-386 (1997).

International Search Report and Written Opinion for PCT/EP2020/057358, dated May 19, 2020.

Odian, G., "Polymer blends and interpenetrating polymer networks," In: Principles of Polymerization, 3rd edition, (New York, Wiley-Interscience) pp. 149-150 (1991).

Pinto, J. et al., "Characterization of the cellular structure based on user-interactive image analysis procedures," Journal of Cellular Plastics, 49(6):555-575 (2013).

* cited by examiner

ABSORBENT ARTICLES HAVING AN ANISOTROPIC FOAM ACQUISITION LAYER

CROSS-REFERENCE TO RELATED APPLICATIONS

This application is the national stage application of corresponding international application number PCT/EP2020/057358, filed Mar. 17, 2020, which claims priority to and the benefit of European application no. 19163535.8, filed Mar. 18, 2019, which is hereby incorporated by reference in its entirety.

TECHNICAL FIELD

The present invention relates to acquisition layers for use in absorbent articles, preferably of the disposable personal hygiene type. Acquisition layers, also called fluid handling layers, liquid-receiving layers or liquid inlet layers, are typically used in absorbent articles to provide additional wicking properties. Disposable personal hygiene absorbent articles herein are typically selected from diapers (for baby or adult incontinence), pants (for baby or adult incontinence), sanitary napkins, sanitary towels, light incontinence towels and pads, and combinations thereof.

BACKGROUND

Flexible open-cell polymeric foams are widely used for energy absorption or insulation (thermal, acoustic, mechanical), filtration, absorption of fluids, and the like. In most cases, the foams desired for these purposes have relatively homogeneous structures comprising cells within a given size range joined by open "windows" or "holes" to adjacent cells. Among the various characteristics of such foams that are important for each application are cell size/hole size and distribution, anisotropy, fraction of material in the struts, porosity and properties of the solid phase. In general, work has been devoted to making foams as homogeneous and isotropic as possible with respect to cell size and shape and density.

Polyurethane (PU) foams having a range of densities are known materials. For instance in the Handbook of Polymeric Foams and Foam Technology edited by D. Klempner and K. C. Frisch Hanser, 1991, flexible PU foams with densities from 16 to 150 kg/m3 and used for seating cushioning, carpet underlayment, fabric backing and or insulation and packaging are described. For example, the "integral skin" flexible polyurethane foams have high density skin layers that transition gradually over 1-3 cm into a lower density core region. See for example Ashida, K.; Iwasaki, K. In Handbook of Plastic Foams", Landrock, A. H., ED.; Noyes, 1995; Chapter 2, pp 56, 64-67, incorporated herein by reference. The overall densities of such foams are typically between about 200 and 1,100 kg/m$^3$. These foams do not exhibit distinct regions having different compositional or microstructural properties within a single piece (i.e. they are homogeneous).

Foams may be made from polymer networks which have been entangled to form an interpenetrating network (IPN). IPNs may exhibit some of the properties of both polymer types. See for example Odian, G. G. "Principles of Polymerization", 3rd edition, Wiley-Interscience: New York, 1991, New York, pp 149-150. IPNs do not inherently relate to control over any features at a supramolecular scale (e.g., density or cell size).

Laminates or sandwiches of two or more layers of foams having differing properties are also well known. See for example, Gibson, L. J.; Ashby, M. F. "Cellular Solids" Pergamon Press: Oxford, 1988, Chapter 9. Formation of such composites requires an additional step and may require use of adhesive which may interfere with the functioning or weight of the foam composite and serves as a potential point of failure.

The development of highly absorbent articles for use as disposable diapers, adult incontinence pads and briefs, and sanitary napkins, is the subject of substantial commercial interest. The ability of such products to acquire, distribute, and store fluids such as are found in body exudates (e.g., urine, sweat, feces, liquid stools, blood and menses) is obviously important to their function. Historically, this has been primarily achieved by using for example, as acquisition and distribution layers, high lofty nonwovens and, as absorbent core, cellulosic fibers and/or superabsorbent particles (generally lightly crosslinked partially neutralized polyacrylic acid that forms a gel when exposed to free water). This approach has, however, encountered a number of difficulties in achieving efficient removal of fluid from the body of the wearer and storage away from the wearer, leading to visible stains (of e.g. menses, liquid stool or urine) on the body facing side of the articles, and in achieving proper flexibility and comfort, i.e. in achieving to provide a product which moves together with the user's movements and which closely follows the shape of the body when being worn.

In the past decade intensive research and development has been carried out in the development of foams particularly designed for disposable personal hygiene products, for example as described in U.S. Pat. Nos. 5,817,704, 5,856, 366, 5,869,171, 6,207,724, US2002128338, and US2005192365. All such attempts have focused on optimization of a number of foam properties, such as capillarity, density, cell size and the like, by particular selection of foams, chemical composition and processing techniques. And these developments have led to successful commercial products such as Always Infinity®, manufactured by the Procter and Gamble Company, having an absorbent core made of two layers of foam having different pore size.

As alternative to products relying exclusively on foams to acquire, absorb and retain body exudates, products have been described having a fluid handling or liquid receiving layer of foam, above a fluid storage or liquid absorbent fibrous layer.

U.S. Pat. No. 6,852,905 discloses a PU foam made from at least an aliphatic isocyanate, and advantageously hydrophilic, as fluid handling layer above an absorbent core of for example fluff pulp and SAP.

US20150328060, US20150313763 and US20150328061 disclose an absorption body including, in its thickness direction, a liquid-receiving, open-cell foam layer and an underneath liquid-absorbent fibrous layer. These documents focus on the relative surface and positioning of these two layers. US20150328061 further teaches that the liquid-receiving, open-cell structure facilitates a rapid admission, and does not need to be very hydrophilic in order to nevertheless function well.

EP3307222 describes a similar structure and teaches to create a plurality of openings in the central region of the liquid inlet foam material to secure that the liquid reaches the absorbent layer of the core below the liquid inlet foam material.

US20150080823 discloses an absorbent composite comprising a first absorbent layer comprising a polymeric foam and a second absorbent layer, that can comprise wood pulp. The polymeric foam is open-celled with a pore size at least 100 microns and is sufficiently hydrophilic to permit the foam to absorb aqueous fluids.

However a need still exists for further specifically optimizing efficient fast absorption of body exudates (which helps in preventing leaks), and reduced rewet (which offers a drier feeling for the wearer), at a reduced cost. Indeed, some of the disadvantages of foam structures of the prior art include complex processes of making as well as high cost.

The present invention is directed at solving the drawbacks still present in the current state of the art.

SUMMARY OF THE INVENTION

In a first aspect, the present disclosure relates to an absorbent article according to claim 1. Such absorbent article comprises a liquid permeable topsheet, a liquid impermeable backsheet, an absorbent core between the topsheet and the backsheet and an acquisition layer between the topsheet and the absorbent core, said acquisition layer having a width and a length along an acquisition plane and a thickness extending perpendicular thereto. The absorbent core comprises at least one absorbent material selected from the group consisting of fibrous absorbent materials and highly absorbent polymers. The acquisition layer comprises a polymeric foam having an open cell and interconnected porous structure comprising an anisotropic cell structure having an axis of anisotropy extending substantially parallel to a longest length of a plurality of substantially neighbouring cells, which is substantially perpendicular to the acquisition plane. The acquisition layer is in direct or indirect contact with the absorbent core.

The product of the present invention overcomes the problems of prior art products, as it provides an efficient directional flow of body exudates within the product and limits the amount of blood, menses urine or liquid stool residues viewable on the first layer when viewed from the body facing side, by providing at the same time a combination of low acquisition time, low rewet and low stain spreading. This is further achieved in a simple and cost-effective way without complex and considerable foam formulation and processing requirements.

Other objects and advantages of this invention will become apparent hereinafter.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. Herein, "comprise" and "include" mean that other elements and/or other steps which do not affect the end result can be added. Each of these terms encompasses the terms "consisting of" and "consisting essentially of".

The expression "in direct contact" means that the elements referred to are touching each other, whilst when using the wording "in indirect contact", the elements are separated by a layer which does not substantially affect the liquid handling of the combined elements, for example a layer of nonwoven, e.g of a core wrap. This intermediate layer is preferably thin compared to at least one of the two elements in indirect contact. The contact surface between the two elements considered may provide direct contact in some regions and indirect contact in some other regions. Advantageously, some adhesive may be present between the two elements in contact. This adhesive may be present as a full surface layer or as a zoned layer, where only regions (e.g. stripes, patterns) have adhesive. The presence of adhesive does not change the definitions of direct and indirect contacts mentioned above; adhesive is simply not considered when assessing if there is direct contact or indirect contact.

"Anisotropy or anisotropic" as used herein means that the element referred to (e.g. the pores or cells of the foam(s)) are elongate in shape (i.e. have a non-uniform, non-homogeneous or non-spherical shape) and comprise one, preferably only one, longest dimension (i.e. a longest length being greater than all other dimensions forming said element). Ideal isotropic elements have an average anisotropy ratio R of 1. Anisotropic elements have an average anisotropy ratio R of greater than 1, preferably greater than 1.1, as measured according to the method described herein.

The expression "% by weight" (weight percent or % wt), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

The expression "absorbent article" or "personal hygiene articles" or "personal hygiene absorbent articles" refers to articles which absorb and contain body exudates or discharges such as body fluids, and is intended to include sanitary napkins, pantiliners, diapers, pants, and incontinence pads (and other articles worn in the crotch region of a garment).

The expression "disposable" refers to articles which are intended to be discarded after a single use, composted, or otherwise disposed of in an environmentally compatible manner. (That is, they are not intended to be laundered or otherwise restored or reused as an absorbent article.)

As used herein, the term "diaper" refers to an absorbent article generally worn by incontinent persons about the lower torso.

The expression "sanitary napkin" refers to articles which are worn by females adjacent to the pudendal region which are intended to absorb and contain the various exudates which are discharged from the body (e.g., blood, menses, and urine).

"Pant" refers to a garment that has a waist opening and a pair of leg openings, similar to shorts, swim wear, or the like. The described garment may or may not have a manually tearable side seam.

The "absorbent medium" or "absorbent core" or "absorbent body" is the absorbent structure disposed between the topsheet and the backsheet of the absorbent article in at least the crotch region of the absorbent article and is capable of absorbing and retaining liquid body exudates. The size and the absorbent capacity of the absorbent medium should be compatible with the size of the intended wearer and the liquid loading imparted by the intended use of the absorbent article. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers or superabsorbent polymer particles (SAP), absorbent nonwoven materials (e.g. nonwoven comprising at least 50% cotton) or the like, or any combination of two or more of these absorbent materials like "airlaid cores", also called "airlaid paper" made of a thin airlaid layer onto which SAP are adhered. It is common to combine cellulosic fluff pulp with superabsorbent polymers in an absorbent material. The absorbent core may comprise one or more layers of absorbent material stacked on top of each other.

The term "topsheet" refers to a liquid permeable material sheet forming the inner cover of the absorbent article and which in use is placed in direct contact with the skin of the wearer. The topsheet is typically employed to help isolate the wearer's skin from liquids held in the absorbent structure. The topsheet can comprise a nonwoven material, e.g. spunbond, meltblown, carded, hydroentangled, wetlaid etc. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. The topsheet material may further be composed of two fibres, which may be bonded to each other in a bonding pattern. Further examples of topsheet materials are porous foams, apertured plastic films, laminates of nonwoven materials and apertured plastic films etc. The materials suited as topsheet materials should be soft and non-irritating to the skin and be readily penetrated by body fluid, e.g. urine or menstrual fluid. The inner coversheet may further be different in different parts of the absorbent article. The topsheet fabrics may be composed of a substantially hydrophobic material, and the hydrophobic material may optionally be treated with a surfactant or otherwise processed to impart a desired level of wettability and hydrophilicity.

The term "backsheet" refers to a material forming the outer cover of the absorbent article. The backsheet prevents the exudates contained in the absorbent structure from wetting articles such as bedsheets and undergarments which contact the disposable absorbent article. The backsheet may be a unitary layer of material or may be a composite layer composed of multiple components assembled side-by-side or laminated. The backsheet may be the same or different in different parts of the absorbent article. At least in the area of the absorbent medium the backsheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The backsheet material may be breathable so as to allow vapour to escape from the absorbent material, while still preventing liquids from passing there through. Examples of breathable backsheet materials are porous polymeric films, nonwoven laminates of spunbond and meltblown layers and laminates of porous polymeric films and nonwoven materials.

"Pulp fluff" or "fluff pulp" refers to a material made up of cellulose fibers. The fibers can be either natural or synthetic, or a combination thereof. The material is typically lightweight and has absorbent properties.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

The term "high-absorbency material" refers to materials that are capable of absorbing at least 10 times their own weight in liquid. The high-absorbency material may comprise absorbent gelling materials, such as highly absorbent polymers which include superabsorbent polymers.

Superabsorbent polymers are water-swellable, water-insoluble organic or inorganic materials capable of absorbing at least about 15 or 20 times their own weight of an aqueous solution containing 0.9 weight percent of sodium chloride. Absorbent gelling materials can be natural (i.e. partially or fully made from renewable resources, and/or biodegradable), synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be used. Synthetic absorbent gelling materials typically are xerogels which form hydrogels when wetted. The term "hydrogel", however, has commonly been used to also refer to both the wetted and unwetted forms of the material. The high-absorbency material may be in any of a wide variety of geometric forms. As a general rule, it is preferred that the high-absorbency material be in the form of discrete particles. However, the high-absorbency material may also be in the form of fibres, flakes, rods, spheres, needles, spiral or semi-spiral, cubic, rod-like, polyhedral, or the like. Conglomerates of particles of high-absorbency material may also be used. The high-absorbency material may be present in the absorbent core in an amount of from about 5 to about 100 weight percent and desirably from about 30 to about 100 weight percent based on the total weight of the absorbent core. The distribution of the high-absorbency material within the different portions of the absorbent core can vary depending upon the intended end use of the absorbent core. The high-absorbency material may be arranged in a generally discrete layer within the matrix of hydrophilic fibres. Alternatively, the absorbent core may comprise a laminate of fibrous webs and high-absorbency material or other suitable means of maintaining a high-absorbency material in a localized area. The superabsorbent material may suitably be included in an appointed storage or retention portion of the absorbent system and may optionally be employed in other components or portions of the absorbent article.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 µm, preferably between 300 to 600 µm, more preferably between 400 to 500 µm.

By the terms "particle", "particles", "particulate", "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

The term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

The term "nonwoven fabric or web or layer" means a sheet material having a structure of individual fibers or threads which are interlaid, but not in a regular manner such as occurs with knitting or weaving processes. Nonwoven fabrics or webs or layers have been formed from many processes such as for example, meltblowing processes, spunbonding processes, and bonded carded web processes.

The expression "body surface" refers to surfaces of absorbent articles and/or their component members which face the body of the wearer, while the term "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

The expression "substantially parallel" as used herein means that the element referred to is within 30°, preferably within 15°, more preferably within 10°, most preferably within 5°, from the axis, plane or element referred to.

The expression "substantially perpendicular" as used herein means that the element referred to is within 30°, preferably within 15°, more preferably within 10°, most preferably within 5°, from the axis, plane or element referred to.

The expression "substantially neighbouring" as used herein means not necessarily directly neighboring (or in contact) but rather within a given area, preferably of 1.5 mm×1.5 mm, more preferably 1 mm×1 mm, even more preferably 800 µm×800 µm, most preferably 600 µm×600 µm. For sake of clarity, said area being on a plane extending parallel to the longest length of the element referred to.

The "whiteness" of a substrate can be quantified by using the L*, a*, b* value on the CIELAB Colour scale. In short, in this scale the L* value defines the lightness and ranges from 0 to 100, with 0 being absolute black and 100 absolute white. A description of the cielab scale system is presented in detail in the experimental section below. The central fluid acquisition zone may in one embodiment have an L* hunter value of at least 90 or higher (for example at least 95, or even at least 97), with the absolute value of each a* and b* being preferably below 1, or even below 0.5 as measured directly on the central fluid acquisition zone of the article. If the central zone has coloured decorations, these values are measured in non-decorated spaces of the central zone.

Figure 7:
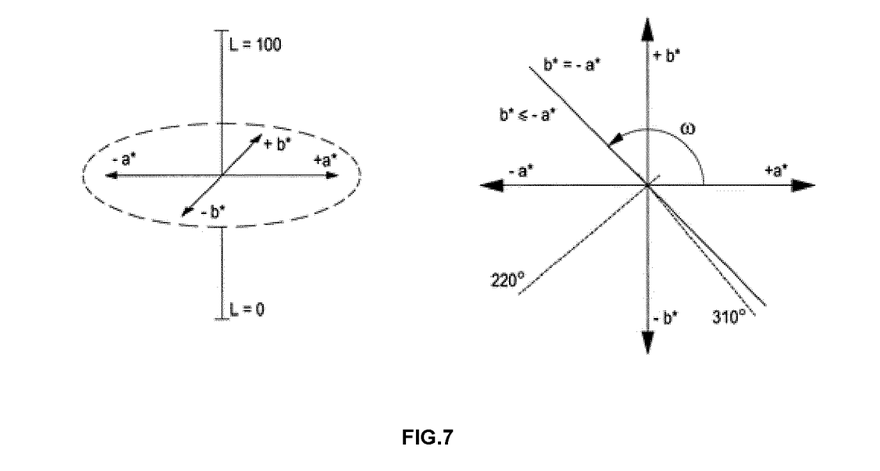
FIG. 7 shows the colour "sphere" used for the representation of colour in the CIELAB system and the horizontal plane of the colour sphere.

The colour of the referred elements (e.g. uppermost surface of first layer of the core) can be characterized by their L*, a* and b* values as measured with the cielab colour scale. It may be preferred that the hue of the colour of the lateral zones may be selected in the blue or green region rather than in the yellow or red region for aesthetic purpose. Furthermore, it has been found that blue and green pigments may better be able to hide underlying stains of blood or urines. Thus the measured a* and b* values may be advantageously such that the relation b*<=-a* is fulfilled. This relation may also be expressed in term of angles values reported to the horizontal colour disc represented on FIG. 7. taking any colour on the +a* axis as having a ω ("omega") angle of 0, any colour on the +b* as having a omega angle of +90° and so forth, and in that case the relation b*<=-a* is equivalent to having a omega angle of from 135° to 315°. It was found that colours in the blue or lilac tone were even more preferable, for which an angle omega of from 220° to 310° is suitable, more precisely of from 257° to 302°.

Embodiments of the articles and processes according to the disclosure will now be described. It is understood that technical features described in one or more embodiments maybe combined with one or more other embodiments without departing from the intention of the disclosure and without generalization therefrom.

The Acquisition Layer

Figure 1:
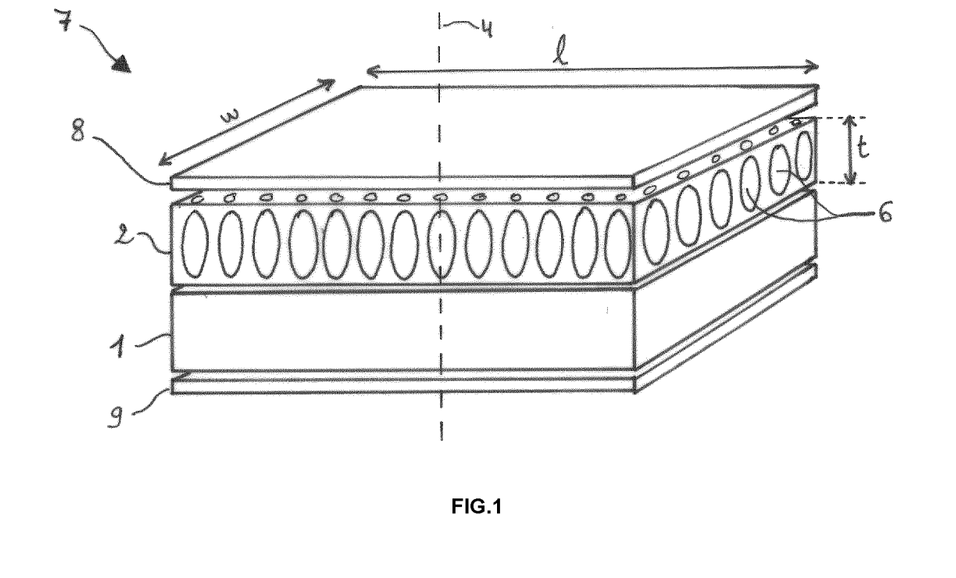
FIG. 1 is a schematic illustration (exploded view) of an exemplary absorbent article according to the present invention.

According to the invention, the acquisition layer 2 is positioned between the topsheet 8 and the absorbent core 1 of the absorbent article 7, and is in direct or indirect contact with the absorbent core 1. Said acquisition layer 2 has a width w and a length l along a plane, which is herein called the "acquisition plane", and a thickness t extending perpendicular to this acquisition plane. The acquisition layer 2 has preferably mostly a planar extension, i.e. a thickness smaller than the other dimensions (width and length). The acquisition layer 2 comprises a polymeric foam having an open cell and interconnected porous structure comprising an anisotropic cell structure having an axis of anisotropy 4 extending substantially parallel to a longest length of a plurality of substantially neighbouring cells 6, which is substantially perpendicular to the acquisition plane.

It has surprisingly been found that introducing foams with anisotropic cell-shaped properties greatly impacts directionality of capillarity, and the exudates are directed in a predetermined manner to directly and quickly flow from the acquisition layer to the absorbent core along the thickness direction. As shown in the examples that follow herein, this brings advantages not only with regards to acquisition time but most importantly excellent resistance to rewet and creation of minimal "blood-spots" on the top surface of the first layer, with the majority of the blood being spread in the absorbent core which is not viewable by the user when in use. A further advantage is the reduced cost versus foam products specifically designed (e.g. via formulation and the like) for achieving similar high levels of performance.

Advantageously, the thickness of the acquisition layer is within a range of 0.5 to 7.5 mm, preferably 1 to 5 mm, most preferably 2 to 3.5 mm.

The width and/or length of the acquisition layer may be identical or similar or different than the width and/or length of the absorbent core. In some advantageous embodiments, the acquisition layer has a smaller area than the absorbent core, in particular to save cost. In such cases, the acquisition layer may be predominantly positioned in the region of the absorbent article intended to directly receive the body exudates, as is known in the art.

In one embodiment, the acquisition layer has a dry-state stress at 5% strain of greater than 1.5 kPa, preferably from 1.7 to 10 kPa, most preferably from 1.75 to less than 2.15 kPa. The mechanical behaviour of the foams is measured in compression at a strain rate of 10 s$^{-1}$ using an Instron Machine (model 5.500R6025). The samples are prepared by forming cylinders of 50 mm in diameter and 10 mm in thickness. The experiments are conducted at 23±2° C. and 50% relative humidity. The samples are conditioned in these conditions 24 hours prior to the experiments. Without wishing to be bound by theory it is believed that if the resistance to compression is about the same or greater than typical stress at sitting position of a user, a reduced rewetting is achieved.

In one embodiment, the acquisition layer has a wet-state stress at 5% strain of greater than 1.0 kPa, preferably greater than 1.50 kPa, more preferably from 1.6 to 8 kPa, most preferably from 1.6 to less than 2.0 kPa. The mechanical tests are performed in a similar way to what described in the previous paragraph but in this case prior to the experiments the samples are immersed in artificial blood (as formulated or prepared by SGS Courtray Laboratories (Oignies, France)) for 1 hour to reach full saturation of the foams. The compressive mechanical tests are then performed on fully saturated samples. Similarly, to the above, by ensuring that also in wet-state, the resistance to compression is about the same or greater than typical stress at sitting position of a user, a reduced rewetting is maintained also when the product is saturated with liquids.

Figure 5:
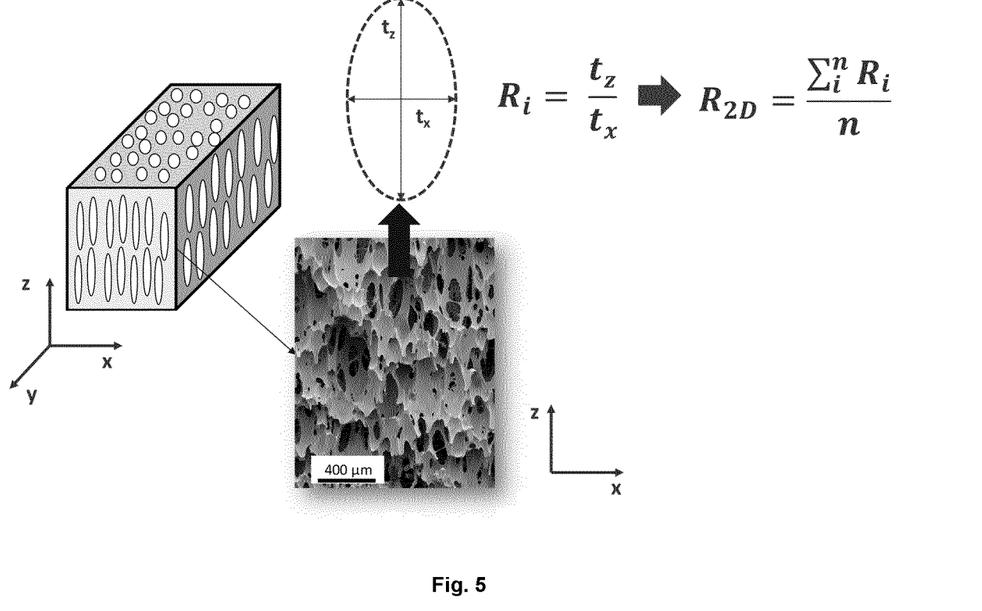
FIG. 5 is an illustration showing how the mean anisotropy ratio R may be determined.
Figure 6:
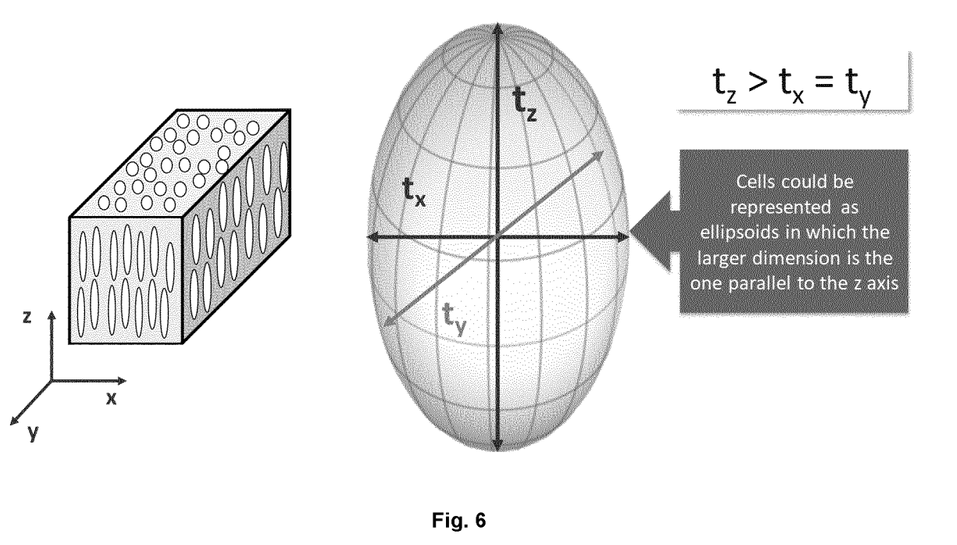
FIG. 6 is an illustration of a typical cell shape of one single cell for a typical foam according to an aspect of the present disclosure.

In a preferred embodiment, the open cells of the foam have an average anisotropy ratio R greater than 1.1, preferably from 1.1 to 3.5, more preferably from 1.2 to 3.0, more preferably from 1.4 to 3.2, even more preferably from 1.5 to 3.1, even more preferably from 1.6 to 3.0, most preferably from 1.7 to 2.5, as measured according to the method described herein. Preferably the anisotropy ratio R in the ranges described above, is for cells having the longest dimension (or length) extending in a direction substantially parallel to the direction that a fluid is expected to travel through a foam layer comprising said cells (for example, for a foam layer comprising a fluid intake axis parallel to the general direction of fluid transport through said layer, the average anisotropy ratio R described above is taken for cells oriented such that the longest length thereof is substantially parallel to said fluid intake axis). An advantage of such arrangement is that directionality of capillarity is enabled along the longest length of the anisotropic cells. FIG. 5 and FIG. 6 schematically illustrate the shape of such anisotropic cells, wherein in two dimensions (shown in FIG. 5) the anisotropic ratio of each cell is given by dividing the longest cell length $t_z$ by the shortest cell width $t_x$ typically being substantially perpendicular thereto. The average anisotropy ratio R is then given by the sum of said ratios divided by the number of cells n measured. Further details on the method used for calculating the average anisotropy ratio is provided herein below. FIG. 6 illustrates a preferred cell shape, being ellipsoidal in shape and having three dimensions. The longest length $t_z$ being greater than the lengths in directions substantially perpendicular thereto $t_x$ and $t_y$. Preferably, lengths $t_x$ and $t_y$ being substantially equal. An advantage of this arrangement is improved directionality of capillarity. Methods on how to achieve such cell geometry are described herein below in the section pertaining to methods of making.

In an embodiment, the foam comprises, preferably consists of, an open cell polymer foam, more preferably foams selected from the group consisting of polyurethane (PU), poly vinyl alcohol (PVA), polyolefins such as low-density polyethylene (LDPE), ethylene-vinyl acetate (EVA), ethylene butyl acrylate (EBA), open cell silicone foams, natural and synthetic rubbers, and mixtures thereof, most preferred being polyurethane foam. These may be either hydrophilic or hydrophobic, at various degrees of hydrophilicity.

In a preferred embodiment the acquisition layer has a porosity of greater than 70%, preferably greater than 80%, more preferably greater than 90%, even more preferably from 92% to 99%, most preferably from 94% to 98%. Porosities are measured according to the method described herein. These values may ensure that the appropriate fluid handling and wicking is achieved in the acquisition layer.

In an embodiment the average cell size of the acquisition layer is from 50 to 750 microns. Average cell size is measured according to the method described herein. An advantage of this embodiment is ensuring a faster flow of liquid from the acquisition layer to the absorbent core, thus ensuring that blood spots or other stains on the first layer are limited.

In an embodiment (not shown), the average cell size and/or porosity in the acquisition layer exhibit a gradient in a direction substantially parallel to the anisotropy axis such that respective average cell size and/or porosity proximal to the upper surface of said acquisition layer (closer to the body facing surface) is greater than the average cell size and/or porosity distal from said upper surface and proximal to the absorbent core. An advantage of said gradient is that further wicking directionality is achieved towards the absorbent core. Such graded porosity may be achieved for example by using traditional freeze-casting methods as the foaming process whereby the polymer is mixed with a solvent (typically water), then frozen such that the solvent in solidifying forms dendrites that compress and separate the dissolved polymer particles in compacted channels, followed by a sublimation step to remove the solidified solvent and a sintering or curing step to finally form the porous structure. In such process, the porosity and pore/cell size may be controlled by controlling the freezing temperature and cooling position, with the dendritic formation varying as the distance from a cooling position is increased (generally with the low porosities and cell sizes being located close to the cooling position and lower cooling temperatures and higher porosities and cell sizes located distal from said cooling position and higher freezing temperatures). Alternatively, such graded porosity and/or cell size may be achieved by laminating together a plurality of layers having different porosity and/or cell size to form a laminated first and/or second layer having such graded structure and/or by using different formulations of foams that are poured into a mould in a consecutive manner promoting layers with different characteristics.

In an embodiment, the foam layer described herein has a density ρ of less than 250 kg/m$^3$, preferably from 15 kg/m$^3$ to 220 kg/m$^3$, more preferably from 20 kg/m$^3$ to 200 kg/m$^3$, even more preferably from 30 kg/m$^3$ to 190 kg/m$^3$. Density is measured using the method described herein.

When the acquisition layer is in indirect contact with the absorbent core, the intermediate layer therebetween is preferably free of foam.

The Absorbent Core

According to the invention, the absorbent core 1 comprises at least one absorbent material selected from the group consisting of fibrous absorbent materials and highly absorbent polymers. It is preferably free of foam.

Fibrous absorbent materials may include synthetic or cellulosic fibres e.g. fluff pulp, tissue layers, absorbent nonwoven materials or the like, or any combination of two or more of these absorbent materials and mixture thereof.

In an embodiment, the absorbent core may be composed of a single absorbent material, preferably being selected from fluff pulp, preferably cellulosic fluff pulp, tissue layers, highly absorbent polymers (e.g. superabsorbent polymer particles or "SAP"), absorbent nonwoven materials, for example to improve production efficiency.

In another embodiment, the absorbent core may comprise at least two different absorbent materials, each absorbent material individually preferably being selected from fluff pulp, preferably cellulosic fluff pulp, tissue layers, highly absorbent polymers (e.g. superabsorbent polymer particles or "SAP"), absorbent nonwoven materials. The at least two different absorbent materials may be homogeneously mixed or may be applied in two or more separate layers. An example of such embodiment is a core comprising fluff, SAP, and an enclosing nonwoven core wrap. In that case the acquisition layer is said to be in indirect contact with the absorbent core.

In an embodiment of a sanitary napkin, the highly absorbent polymers are comprised at a level of at least 5% wt, preferably at least 10%, more preferably more than 20%, by weight of the absorbent core. Preferably, the weight ratio (by weight of the absorbent core) of the highly absorbent polymers and the fibrous absorbent materials is less than 20:80, preferably less than 15:85.

In an embodiment of a baby diaper, the highly absorbent polymers are comprised at a level of at least 50% wt, preferably at least 60%, more preferably more than 70%, by weight of the absorbent core. Preferably, the weight ratio (by weight of the absorbent core) of the highly absorbent polymers and the fibrous absorbent materials is more than 60:40, preferably more than 70:30; it can range from 71:29 to 100:0.

To further improve liquid distribution within the absorbent core, the absorbent core according to the invention may comprise substantially continuous zones of one or more high fluid distribution structures and discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures.

For example the absorbent core according to the invention may comprise zones or lines of absorbent material having a density which is lower than the density of the one or more first zones or lines of absorbent material, e.g. the bulk density of the bulk absorbent material. The positioning of the zones or lines of absorbent material having a lower density in the absorbent core may be varied to provide channels for fluid distribution in the absorbent core. The zones or lines of absorbent material having a lower density providing channels for fluid distribution in the absorbent core may be positioned in any direction in the absorbent core to optimize the fluid distribution through the absorbent core, as for example described in WO2018167146 A1, in particular p.14 l.1 to p.15 l.7 and p.17 l.13 to p.23 l.7.

As another example the absorbent core according to the invention may comprise one or more channels having a first shape when the absorbent core is in dry state and a second shape when the absorbent core is in wet state and wherein said first and second shapes are different. Preferably the continuous zones of one or more high fluid distribution structures extend along a path that is substantially parallel to at least a portion of the perimeter of the core, said portion of the perimeter of the core comprising at least a portion of the longitudinal sides of the core and one of the ends of the core. Such types of absorbent cores are for example described in WO2018122117 A1 from p.27 last paragraph to p.28 l.2. One example of such embodiment is a core comprising fluff and SAP enclosed between a top core wrap layer and a bottom core wrap layer, wherein at least one channel is formed as a zone comprising substantially no fluff and SAP, along which the top and bottom core wrap layers are joined together, e.g. by an adhesive. In such example, the acquisition layer of the invention is in indirect contact with the absorbent core through a top core wrap layer.

The Absorbent Article

The absorbent article 7 according to the present disclosure comprises an absorbent core 1 and an acquisition layer 2 as described herein, wherein the absorbent article 7 further comprises a liquid permeable topsheet 8 and a liquid impermeable backsheet 9 with said acquisition layer 2 and absorbent core 1 being sandwiched therebetween, such that the absorbent core 1 is between the topsheet 8 and the backsheet 9 and the acquisition layer 2 between the topsheet 8 and the absorbent core 1.

It may be advantageous that the absorbent article 7 further comprises a non-woven layer between the acquisition layer 2 and the absorbent core 1. This may offer an improved distribution of the liquid, to transport the body fluid away from the initial impingement zone and use as much as possible the whole surface of the absorbent zone of the article. In this configuration, the liquid flow may be better promoted from the acquisition layer to the additional non-woven layer and subsequently, when entering said layer at the point of influx, is spread laterally across a plane parallel to the acquisition plane in said non-woven layer. The additional non-woven layer being also in fluid communication with the absorbent core below, a majority of the total surface area of the core may be used to store the liquid. This embodiment may ensure minimal saturation of the acquisition layer (thus reducing visible stains on the body facing side) whilst maximizing saturation of the additional non-woven layer and the absorbent core.

The width and/or length of this non-woven layer may be identical or similar or different than the width and/or length of the acquisition layer and/or of the absorbent core. In some advantageous embodiments, this non-woven layer has an area similar to the area of the acquisition layer and smaller than the area of the absorbent core.

In an embodiment, the topsheet 8 or the uppermost surface of the acquisition layer 2 closest to said topsheet 8 comprises a coloured area comprising a colour pigment imparting a hue having a w angle measured in the CIELAB colour scale of from 135° to 315°, and preferably said coloured area having an opacity of at least 20%, preferably at least 30%, more preferably at least 40%, most preferably at least 50%, as measured according to the method described herein. An advantage of this embodiment is that further masking of the menses residues is achieved thus limiting its viewability from the body facing surface of the article.

Preferably, said coloured area extends through the entire surface of the topsheet 8 or the acquisition layer 2; or is located in a central portion of said absorbent article 7 and distal from perimeter edges thereof, preferably said coloured area being positioned such that when said article 7 is worn by a subject the coloured area is proximal to a genital opening through which body fluids are expelled. An advantage of this embodiment is that the masking effect is localized on where it is needed with this particular construction. Indeed, the acquisition layer described herein enable a restricted menses residue spot in the area that comes in close contact with the fluid outlets without substantial propagation or wicking in directions parallel to the acquisition plane, whilst in the absorbent core (closer to the garment side) wicking in directions parallel to the acquisition plane occurs to better trap the liquid therein since such layer being on the garment side of the article is not viewable by the user.

In an embodiment, the coloured area is substantially circumscribed by a non-coloured area. This has the advantage of creating a visual perception of performance in the region of typical saturation.

In an embodiment, the acquisition layer 2 comprises one or more interconnected macro channels. Preferably, said macro channels are positioned at least on the upper surface of the acquisition layer 2, said upper surface being opposite the absorbent core 1, and extending at least a portion of the length l and width w of said acquisition layer 2. The macro channel may form a recess within the acquisition layer 2 having a predetermined depth. By "macro channel" as used herein, it is intended that the channel referred to has a length of greater than 1 cm and a width of greater than 2 mm, and preferably a depth of greater than 0.5 mm. Wherein, the depth is parallel to an axis perpendicular to the acquisition plane and wherein the length and width are along a plane parallel to the acquisition plane. An advantage of this configuration is that liquids (e.g. menses or urine) can more effectively and quickly be distributed over the acquisition layer and also to account for deformation of the foam upon swelling in wet conditions so as to retain its general overall shape and limit excess deformation that could lead to discomfort when worn by a subject.

In a preferred embodiment, the one or more macro channels are interconnected such that liquid is distributed therethrough without liquid build-up. Preferably, substantially the entire channel surface is coloured (with a colour different from the rest of the absorbent core) and exhibits the Opacity levels described in the above paragraphs. An advantage of this arrangement is to provide masking of stains in the location where most needed, as well as providing a perception of added depth and absorption of the product.

In an embodiment, the acquisition layer comprises at least one zone differing in stiffness, said zone comprising at least one portion where foam material is not present or has been removed. Said portion defines at least one aperture, which may be of any shape, e.g. circular, ellipsoidal, rectangular, slit, slot. Such zone may provide additional comfort and flexibility, and/or account for deformation of the foam upon swelling in wet condition. The aperture preferably extends across the entire thickness of the foam acquisition layer.

Figure 2:
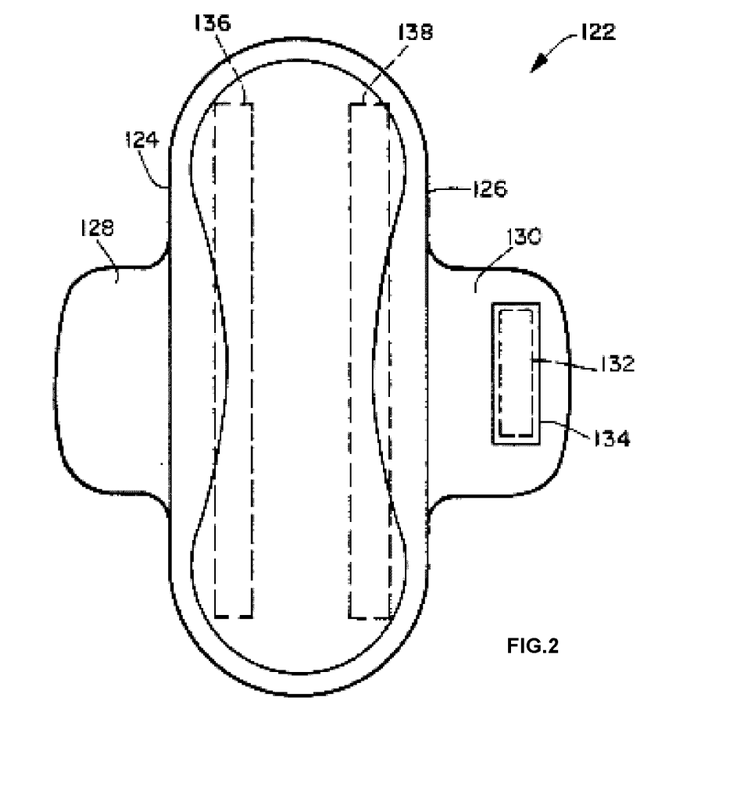
FIG. 2 is a top plan view of a disposable absorbent article, a sanitary napkin, which is one embodiment of the present disclosure.

FIG. 2 is a top plan view of a further exemplary embodiment of a disposable absorbent article 122 (more particularly a sanitary napkin) which is one embodiment of the present disclosure. The absorbent article typically comprises a liquid impermeable backsheet having a garment facing side and a body facing side opposite thereto, a liquid permeable topsheet positioned on the body facing side of the backsheet, an absorbent core positioned between the backsheet and the topsheet, and an acquisition layer positioned between the topsheet and the absorbent core. The acquisition layer may comprise a foam structure as described herein, and the absorbent core may comprise cellulosic fibers and/or super absorbent polymer particles. The core may further comprise a nonwoven (or tissue paper) wrap that encloses said fibers and/or particles therein. The absorbent article 122 may further comprise opposed side edges 124, 126 extending substantially parallel to a longitudinal length of the absorbent article 122 that are typically perpendicular to a width of the absorbent article. Optionally, the absorbent article 122 may comprise one or more wings 128, 130 on at least a portion of each of the side edges 124, 126.

The absorbent article 122 may further comprise one or more first adhesive regions 136, 138 on the garment facing side of the backsheet that typically extend along the length of the absorbent article 122. Such first adhesive regions may be adapted to adhere to a wrap sheet arranged to form a pouch enclosing the absorbent article 122 and after removal of said wrap sheet adhere to a garment surface of the underwear of the wearer. Optionally, when the absorbent article comprises one or more wings 128, 130, each said wing 128, 130 may comprise a second adhesive region 132 on the garment facing side and arranged to adhere to a garment surface of the wearer. In this embodiment, the absorbent article 122 comprises at least one (preferably two) protective strip 134 over the second adhesive region 132 to prevent it from adhering to the wrap sheet forming the pouch enclosing the absorbent article 122 when in the pre-use folded position (i.e. in the individually wrapped state prior to use/opening).

In an alternative embodiment (not shown), the absorbent article may be a pant or a diaper (whether for babies or adult incontinence) or a light incontinence towel or pad.

The Process of Making

A method of making acquisition layers as described herein, may comprise the steps of: (i) providing a mixture comprising one or more reactants and/or polymers; (ii) placing said mixture in a mould and applying or generating in-situ one or more fluid substances (typically a gas) such to promote a non-uniform cell growth that typically leads to an anisotropic cell structure (this is preferably achieved by using a mould with a single open end such that cell growth is promoted along an axis crossing said opening during a foaming step to provide a foam comprising an anisotropic cell structure, typically having an anisotropic axis extending through said opening. It is however understood that other methods my equally be used in order to achieve such non-uniform cell growth without departing from the teaching of the present disclosure); (iii) forming a foam block by solidifying said mixture; (iv) demoulding the foam block.

In an embodiment, the process for making acquisition layers described herein comprises the steps of: (i) mixing a formulation comprising a first water based component preferably comprising one or more surfactants, or a first polyol based component comprising water and a second isocyanate based component, such that mixture creates a gas phase and a polyurethane-based polymeric matrix; (ii) placing said mixture in a mould having a single open end such that cell growth is promoted along an axis crossing said opening during a foaming step to provide a foam comprising an anisotropic cell structure; (iii) demoulding the foam block.

Figure 3:
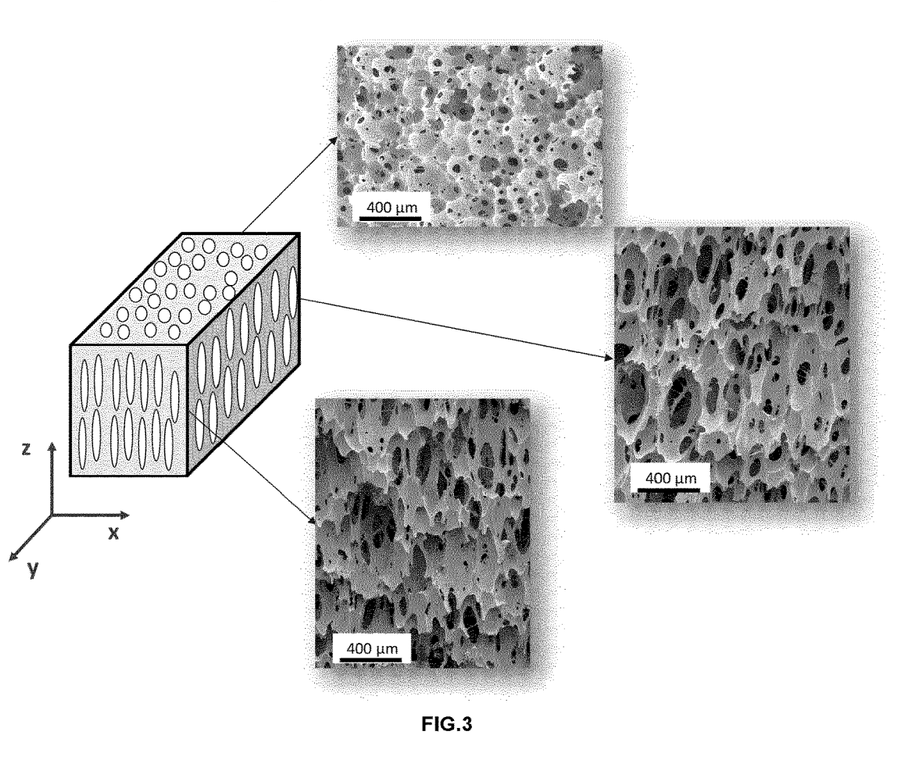
FIG. 3 is a schematic representation, including exemplary SEM images, shown in three planes of an open cell foam block according to an embodiment of the present disclosure.

FIG. 3 shows schematically (and further with Scanning Electric Microscope (SEM) images) the cells structures obtained by following the above method. As can be observed, the controlled cell growth in one direction ensures that a resulting foam block has isotropic shaped cells in planes parallel to the x-y plane and substantially anisotropic shaped cells in planes parallel to the z-x plane and z-y plane.

Figure 4:
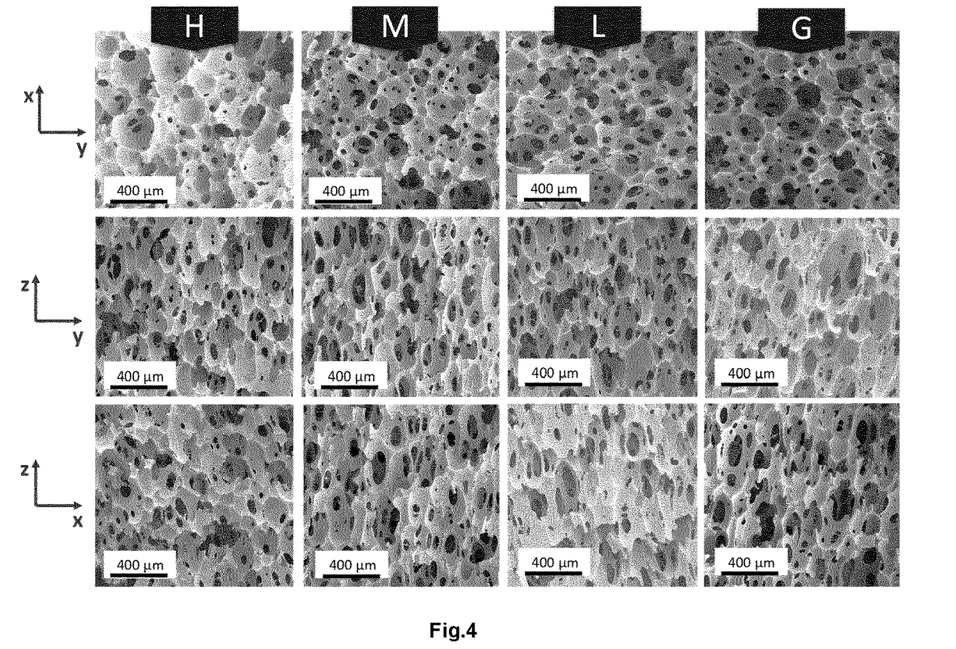
FIG. 4 SEM images taken from some exemplary foams according to an aspect of the disclosure showing different cellular structures in different planes.

FIG. 4 shows schematically (and further with SEM images) different cell shapes for different foams obtained at the various indicated planes of the respective foam blocks. As can be observed from the images, the method described herein is consistent in providing foam blocks H, M, L and G having isotropic shaped cells in the x-y plane and anisotropic shaped cells in the z-x and z-y planes. Cell size and anisotropy ratio can be controlled by different approaches. Cell size can be modified by using nucleating agents, and the type and amount of surfactant and/or modifying the mixing conditions of the reactants. Anisotropy ratio can be controlled by modifying the viscosity of the initial materials and/or the relative speed of the blowing and gelling reactions and/or the cell nucleation mechanisms, all being common in the art of foam making. It is understood that such parameters may be changed according to the desired needs without departing from the teaching of the present disclosure.

Advantageously the resulting foam block has a thickness in the z direction, i.e. in the foam growth dimension, which is also the axis of anisotropy of the cell structure, which corresponds to the thickness t of the acquisition layer. Alternatively, the method of making acquisition layers as described herein may comprise, after the demoulding step, the following additional step: cutting the foam block along at least one first cutting plane, substantially perpendicular to the cell growth and the anisotropic cell structure, to generate a first foam layer, and optionally repeating said cutting step until substantially the entire foam block is cut into foam layers.

In traditional foam making processes, nucleating agents, such as talc, mica calcium carbonate, nanoclays, and the like, are typically used in order to increase cell nucleation. However, in the present disclosure, the inventors have found that by eliminating such nucleating agents, and thus rather promoting cell growth or a small number of large cells, improved anisotropic shaped cells can be achieved which are found to be most beneficial in the arrangements described herein. Thus, in a preferred embodiment, the formulation is free of nucleating agents such as talc, mica calcium carbonate, and nanoclays.

The present invention also pertains to a method of making an absorbent article as herein described, the method comprising the steps of:

(i) providing an acquisition layer having a width (w) and a length (l) along an acquisition plane and a thickness (t) extending perpendicular thereto, said acquisition layer comprising a polymeric foam having an open cell and interconnected porous structure comprising an anisotropic cell structure having an axis of anisotropy extending substantially parallel to a longest length of a plurality of substantially neighbouring cells, which is substantially perpendicular to the acquisition plane;

(ii) laminating said acquisition layer between a liquid permeable topsheet and an absorbent core, and further with a liquid impermeable backsheet, preferably such that the acquisition layer (2) is in direct or indirect contact with the topsheet and the absorbent core (1), and the absorbent core (1) is in direct or indirect contact with the acquisition layer and the backsheet.

Test Methods

Relative density ($\rho_{rel}$): It is defined as the density of the foamed material ($\rho_f$) divided by the density of the solid material before foaming ($\rho_s$). Density of foamed samples ($\rho_f$) is measured as described in ASTM D1622/D1622M-14. In this method samples with a defined geometry are cut from the foamed block and its dimensions and weight are obtained using a caliper with a precision of 0.01 mm and a balance with a precision of 0.01 mg. Density is obtained as the ratio between the mass and the volume of each sample.

Density is determined in three different samples for each material, with a diameter of 30 mm and a height of 25 mm.

Porosity (P): It is volume fraction (in percentage) of the gas phase within the material (e.g. the foam). It is calculated using the following equation (in other words also, 100 times, one minus the relative density):

$$P = 100\left(1 - \frac{\rho_f}{\rho_s}\right)$$

The density of the solid material for 100% open cell foam is measured by using gas pycnometry technique following ASTM D6226-05 In this method the weight of the sample is measured using a balance with a precision of 0.01 mg. Then the volume of the solid phase is measured using a gas pycnometer, in our case we have used nitrogen gas for all the measurements. The equipment used is a gas pycnometer Accupyc II 1340 from Micromeritics. The density of the solid material is obtained as the ratio between the weight of the sample and the volume of the solid phase measured by the gas pycnometer. In the particular case of PU based foams the density of the solid phase was 1160 kg/m3.

Average cell (or pore) size: Three (3) samples of each foam layer are cut into squares of 5 by 5 mm in size. Each sample is vacuum coated with a gold thin layer (a few nm thick) and the cellular morphology of the foams is observed by Scanning Electron Microscopy (SEM) with a JEOL JSM-820 microscope. Each sample is examined by SEM on each of the planes xy, xz, and yz (as shown schematically in the figures herein) by taking at least 3 SEM micrographs in random locations from each plane. An image analysis technique is then used according to and as described in "Characterization of the cellular structure based on user-interactive image analysis procedures" [Pinto J, Solorzano E, Rodriguez-Perez M A, and de Saja J A. *Journal of Cellular Plastics* 2013; 49(6):555-575.], herein incorporated by reference, for each of the SEM micrographs to determine the main characteristics of the cellular foam structure: average cell (pore) size ($\phi$), and average anisotropy ratio (R).

As it is indicated in the cited reference, the method gives quantitative results virtually identical to the standard method ASTM D3576-04 Standard Test Method for Cell Size of Rigid Cellular Plastics with the added benefit of providing a more detailed description of the cellular structure of the materials.

The average cell size and anisotropy ratio are measured for each plane of the foam (xy, xz and yz). In this way three averages cell sizes (one per plane) and three anisotropy ratios (one per plane) can be obtained for each foam. In the next paragraphs we explain how these parameters are measured for one plane. The description is for the xy plane, but the same method is repeated for the other two planes.

Figure 9:
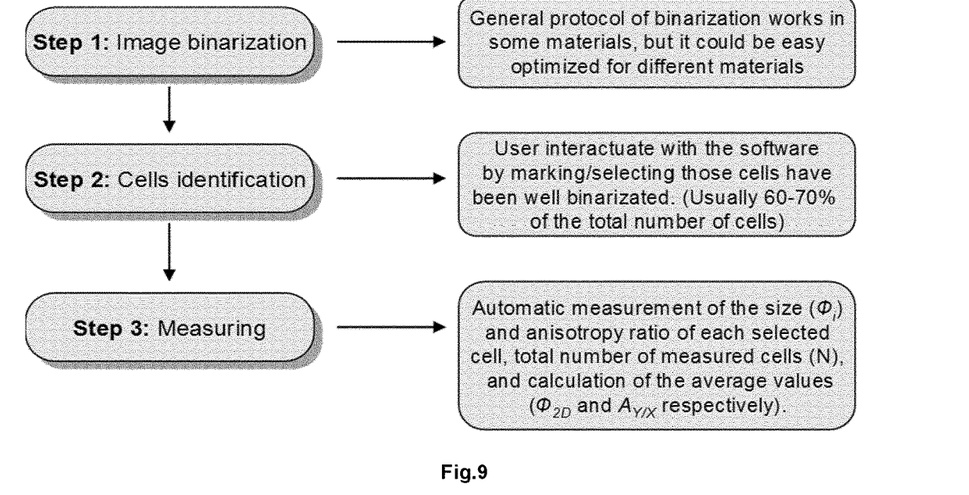
FIG. 9 is a flow diagram of a method used to measure the average cell size and the average anisotropy ratio, according to an aspect of the disclosure.
Figure 10:
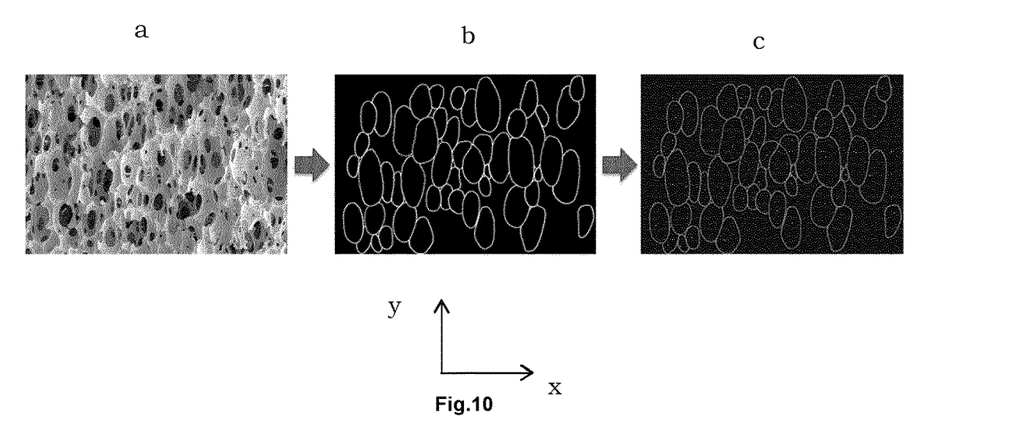
FIG. 10 exemplifies the micrograph processing: a) original SEM image; b) binarization of the image; and c) selection of the cells to measure the average cell size and the average anisotropy ratio according to the methods described herein.

A schematic flow diagram of the method is shown in FIG. 9, summarizing the description of the process. First step is the binarization of the micrographs, in the general process the image contrast is enhanced and a median filter is applied to reduce the noise of the image and preserve edges, then a convolve filter is applied to obtain an image where the edges are revealed. From this a binary image of the cell walls is obtained (FIG. 10).

Every binarized micrograph could present some defects, voids that are not cells, broken cell walls and incomplete cells in the image borders. These defects are source of inaccuracy for the cellular structure characterization if an automatic cell identification process is used. This is the reason why a user-interactive cell identification process is implemented. It basically consists in a user selecting/validating the cells with no binarization/border defects which subsequently will be measured (see FIG. 10-*c*, with selected cells having dots in the center).

This process allows to measure a significant number of cells, in images with an appropriate magnification (around 150-200 cells per image) it is possible to measure around a 60-70% of the cells.

Each selected cell is measured following this procedure: first the center of the cell is selected, Subsequently, from this point it measures the cell diameter in eight different directions (angles), obtaining the bidimensional cell size in eight different directions. From these measurements, the cell size of each single cell is obtained by averaging the eight values obtained. Anisotropy ratio of each single cell is measured as the ratio between the cell size (diameter of the cell) in the y direction of the image and the cell size (diameter of the cell) in the x direction.

Once the values of the cell size and the anisotropy ratio of each single cell is measured the average value of these parameters for the collection of n cells measured are obtained. These are the parameters denominated as Average cell (or pore) size and Average anisotropy ratio (R) herein.

For all the foams characterized herein the cell size and anisotropy ratio of a minimum of 200 cells are determined to obtain representative average values of both parameters.

Opacity: A dispersion colorimeter is preferably used for determining the opacity of a sample material. A preferred dispersion colorimeter is available from BYK-Gardner GmbH, Geretsried, Germany, under Trade Name "BYK Gardner Color-Guide 45/0" (Cat. No. 6800).

The measurements should be conducted by using a light source "A" at a viewing angle of 2° (degrees). This dispersion colorimeter includes a light source for Illuminant A (i.e., an approximation of incandescent lamp having a correlated color temperature of about 3000 K), a flat table, a white standard plate, a standard black plate, a photo detector which includes a multi- celled photo-detector diode array, and a computer. The white and black standard plates are available from the same company under Cat. Nos. 6811 and 6810, respectively. In the measurement, the white standard plate is placed on the flat table. A sample material is put on the white standard plate in a flat state. The sample material is illuminated by the light source with an incident angle of 45°. The reflection light which is reflected from the sample material is received by the photo detector with a receiving angle of 0°. The reflection rate (Yw) of the reflection light is detected by the photo detector. Similarly, after the black standard plate is placed on the flat table, the sample material is put on the black standard plate in a flat state. The sample material is illuminated by the light source with an incident angle of 45°. The reflection light which is reflected from the sample material is received by the photo detector with a receiving angle of 0°. The reflection rate (Yb) of the reflection light is detected by the photo detector. The opacity (OP) is obtained by the following formula:

$$OP\ (\%) = (Yb/Yw) \times 100 \quad (1)$$

This process is repeated for one sample sheet material at least five times and the average value of the opacities (OP) measured is calculated and recorded by the colorimeter. The average value of the opacities measured is called the opacity of a sheet material.

EXAMPLES

Example 1 is a sanitary towel comprising in sequence: a perforated non-woven topsheet 24 gsm commercially available from Texol (product code N03C24049); a foam acquisition layer 210 gsm commercially available from Contec® (product name: FoamZorb™—https://www.contecinc.com/la/products/foamzorb/) having a thickness of 3 mm and comprising a PU foam having an open cell and interconnected porous structure comprising an anisotropic cell structure; an absorbent core comprising cellulosic fluff fibers and super absorbent particles (Ultra fluff towel, manufactured by Ontex®) commercially available from Ontex bvba; and a polyethylene non-breathable backsheet 25 gsm. The acquisition layer has the same area as the absorbent core, and therefore covers the entire area of the core.

The foam has been positioned in the towel to ensure that its axis of anisotropy is substantially perpendicular to the acquisition plane, i.e. vertical compared to the horizontal plane in which the sanitary towel lies. The foam has a dry-state stress at 5% strain of 3.8±0.22 kPa and a capillarity along the axis of anisotropy of 0.9±0.09 mm.

Example 2 is identical to Example 1, except that the absorbent core has been replaced by a different absorbent core also comprising cellulosic fluff fibers and super absorbent particles, but additionally comprising multiple zones comprising different amounts of absorbent material, showing improved body fit and fluid distribution, as described in WO2018167146 A1 in the embodiment of FIGS. 6a and 6b.

Comparative Example 1 is identical to Example 1, except that the acquisition layer has been replaced with a foam layer having a thickness of 2 mm and a basis weight of 468 gsm, prepared by a reactive foaming process starting from an isocyanate based prepolymer phase commercially available from Dow® under the brand HYPOL™, which comprises a PU foam having an open cell and interconnected porous structure comprising an anisotropic cell structure. The foam has a dry-state stress at 5% strain of 1.8±0.12 kPa and a capillarity along the axis of anisotropy of 2.9±0.11 mm.

The foam has been positioned in the towel to ensure that its axis of anisotropy is substantially parallel to the acquisition plane, i.e. horizontal, just like the horizontal plane in which the sanitary towel lies.

The foamed samples are prepared by the reactive foaming process, that is, by reacting a mixture of two components: a hydrophilic isocyanate based prepolymer phase and water-based component inside a mould (the ratio of the two components in the mixture is 1:1). The reaction of these two components promotes on the one hand, the generation of a gas phase, which expands the viscous mixture and constitute the interior of the cells in the final foam, and on the other hand, the subsequent polymerization of the PU-based solid phase which in the end constitutes the cell walls and struts of the foam. The foam expansion takes place in the z (height) direction of the mould.

The isocyanate based prepolymer phase used in this example is HYPOL™ which is the brand commercially available from Dow®. Distilled water is used as the water phase. Water phase is pre-cooled at 15° C. and the prepolymer is maintained at room temperature before the mixing process. Both components are poured inside a plastic container and thoroughly mixed by a shear mixer (IKA EUROSTAR 60) at a constant speed (1500 rpm) and for 10 seconds. Shortly after, the mixture is poured into the bottom of a prismatic mould with the following dimensions: 20 (height)×10 (width)×10 (thickness) cm, which restricts the expansion of the foam to the height direction. The reaction between both components, which is exothermic, starts, which implies the generation of the gaseous phase, the expansion of the viscous mixture and the polymerization of the solid phase. After about 120 seconds, or time enough to complete the reaction process, the foam fills completely the mold and becomes stable. A foamed block with the following dimensions is obtained: 20×10×10. The restriction of the expansion to one direction because of using the previously described mould promotes the generation of anisotropic cellular structures in which cells are oriented parallel to the height direction of the foamed block.

The process to produce hydrophilic PU foam, as described here, leads to the presence of a water excess in the solid phase, hence, the foamed block obtained is subjected to drying in a convection oven at 70° C. for a period of time until reaching a water content of less than 0.5% in the final foam (the water content in the foam is measured by gravimetry: weight of the foamed block before drying—weight of the foamed block after drying/weight of the foamed block before drying).

Comparative Example 2 is identical to Example 1, except that the acquisition layer has been replaced by a foam layer taken out of ultra thin pads with flexible fit, with Technocel Foam Core, size normal, 18 pads, commercialized by CVS Health, and bought in the US before November 2017, product code: 300111. Said foam layer comprises a PU foam having an open cell and interconnected porous structure comprising a substantially isotropic cell structure. Its basis weight was 51.4 gsm and thickness around 1.6-1.7 mm.

Comparative Example 3 is a sanitary towel commercially available by the Procter & Gamble Company, under the brand Always® Infinity, with smart foam, size normal, 10 pads with wings, and bought in Israel before September 2017, product code: 5287478600 62 13 28 20151015. This product comprises a liquid permeable topsheet, a liquid impermeable backsheet, and an absorbent core between the topsheet and the backsheet, said absorbent core being made of two distinctive foam layers mainly differing by the cell size. The two layers of foam comprise an acrylic foam having an open cell and interconnected porous structure comprising a substantially isotropic cell structure. The foam has a dry-state stress at 5% strain of 1.9±0.28 kPa and a capillarity of 2.0±0.17 mm.

The various foams of the five above products have been characterized and their average anisotropy ratio R and average cell size have been measured (using the methods previously described). Table 1 shows the results of these measurements.

TABLE 1

|  | Examples 1 and 2 | Comp. Ex. 1 | Comp. Ex. 2 | Comp. Ex. 3 |
| --- | --- | --- | --- | --- |
| average anisotropy ratio R | 1.88 | 2.30 | 1.09 | 1.02 (toplayer) 1.03 (bottom layer) |
| average cell size | 453.8 | 254.6 | 486.5 | — |

The five above products have been subjected to the following tests: acquisition time test, rewet, and stain spreading in length, which are described hereinbelow. The acquisition time test evaluates the speed at which an absorbent article absorbs liquid; lower acquisition times are preferred. The rewet test measures the liquid retention capacity of the article; lower rewet values are preferred. The stain spreading in length indirectly measures the size of the blood spot on the acquisition layer and within the absorbent core by measuring the ratio between the length occupied by the blood spot seen from the upper view (topsheet) or the lower view (backsheet), and the total length of the absorbent core;

lower spreading values on topsheet side, combined with higher values on backsheet side are preferred. Table 2 shows the results of these tests for the present 2 examples and 2 comparative examples.

Acquisition Time and Rewet Measurement
Material
Balance accurate to 0.01 g
Test solution: Synthetic Courtray blood, as formulated or prepared by SGS Courtray Laboratories (Oignies, France). This fluid has a viscosity of 7-8 cPa (Target 7.5 cPA) measured at a temperature of 21° C. using a falling ball type viscosimeter (Category number V-2200, size 2, K value 3.3) with a glass ball.
Electronic timer, scale graduation 1 s
Chronometer
Automatic pump
Plexiglass plate 20×10 cm with thickness of 0.5 cm
2 weights of 1.0 kg (+/−0.02 kg)
Plate with dimensions 20×30 cm, provided in its centre with a tube having a height of 5.5 cm and an inside diameter of 2.2 cm
filter paper Whatman n°4 with dimensions 9×14 cm
at least 2 samples of hygienic towels to be tested.
Procedure
Adjust the automatic pump at a speed rate of 10 ml/min and set the correct volume according to the type of product (4 cm³ for normal size, 7 cm³ for super size). In the present examples, 7 cm³ were used.
Put the plate with the tube in the middle of the product (if the product has wings, place the tube centrally between the wings) and start the pump and measure the time needed with a chronometer for the towel to absorb the synthetic blood (=T1).
Remove the tube and set a timer for 10 minutes.
Put the plate back on the product and pour again the correct amount of synthetic Courtray blood in the tube, and measure the time needed with a chronometer for the towel to absorb the fluid (=T2).
Remove the tube and set a timer for 10 minutes
Put the plate back on the product and pour again the correct amount of synthetic Courtray blood in the tube, and measure the time needed with a chronometer for the towel to absorb the fluid (=T3).
Remove the tube and set a timer for 10 minutes
In the meantime: weigh 8 filter papers (=DW1)
After the 10 minutes: put the filter papers on the product, together with the plexiglass plate and put a weight of 1 kg on it for 10 minutes.
Weigh the wet filter papers (=WW1)
Repeat with the second sample
Calculations
Calculate the acquisition time, given in seconds: TT=T1+T2+T3
Calculate rewet, given in grams: Rewet=WW1−DW1
The ultimate values (as given in Table 2) are the averages of the at least two samples.
Stain Spreading in Length Measurement
Centrifuge the samples having been subjected to the rewet test above, for 3 minutes on 440G.
Weigh and note the weight after centrifugation, to make sure no liquid or matter has escaped from the product
Measure the maximum extension of the stain along the direction of the length of the product, once as viewed on the topsheet (TS), the other as viewed on the backsheet (BS), and divide the results by the total length of the absorbent core. The ultimate values (as given in Table 2) are the averages of the at least two samples, given in %.

TABLE 2

| | | Example 1 ° | Example 2 * | Comp.Ex. 1 ° | Comp.Ex. 2 ° |
|---|---|---|---|---|---|
| Acquisition time | [s.] | 141.5 | 132 | 288.0 | 141.3 |
| Rewet | [g] | 3.58 | 1.51 | 3.81 | 4.23 |
| spreading in length [%] | TS | 27 | 32 | 35 | 32 |
| | BS | 63 | 76 | 41 | 68 |

\* average values over 2 samples
° average values over 6 samples

As demonstrated by the examples, products according to the present invention provide an efficient directional flow of blood through the product and limit the amount of blood residues viewable on the first layer when viewed from the body facing side. They provide at the same time a combination of low acquisition time, low rewet and low stain spreading. This is further achieved in a simple and cost-effective way, with less foam (indeed foam is more costly than the mix of fibrous absorbent materials and absorbent polymer particles forming the herein absorbent core) and without complex and considerable foam formulation or further foam treatment. Example 2, with the specific absorbent core structure including zones with less absorbent material, shows further improved properties, especially rewet. Not wishing to be bound by theory, this may be explained by the property of such absorbent core to provide enhanced fluid distribution.

The comparison between example 1 and comparative example 1, shows the specific advantage of having a foam with an axis of anisotropy which is substantially perpendicular to the acquisition plane, i.e. vertical in the final product. Comparative example 1, having a foam with an axis of anisotropy which is substantially parallel to the acquisition plane, i.e. horizontal in the final product, indeed shows particularly poor acquisition time.

The comparison between example 1 and comparative example 2, shows the specific advantage of having a foam which is anisotropic. Comparative example 2, having a foam substantially isotropic, indeed shows particularly poor rewet.

Finally, comparative example 3, which is a commercially available product, provides poor acquisition time.

Figure 8:
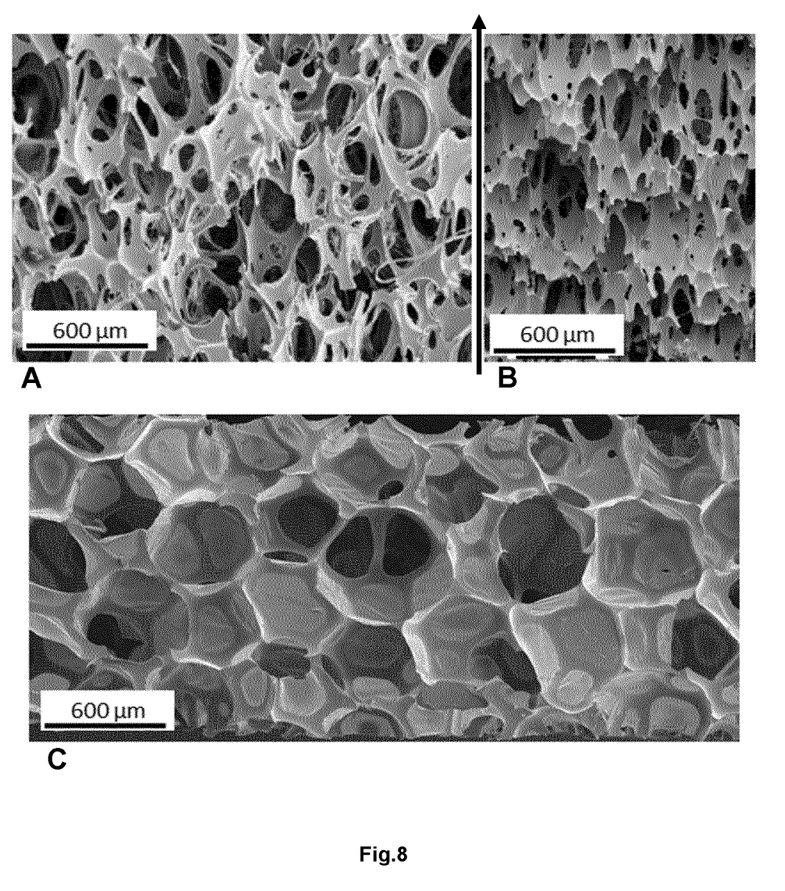
FIG. 8A SEM image of the foam of examples 1 and 2 (the arrow represents the axis of anisotropy)
FIG. 8B SEM image of the foam of comparative example 1 (the arrow represents the axis of anisotropy)
FIG. 8C SEM image of the foam of comparative example 3

Capillarity Measurements: For the capillarity measurements, the dried foamed block previously described in comparative example 1 are sliced into three different types of layers (EXAMPLE A, B and C), all of them with 0.2 cm in thickness, 20 cm in length and 5 cm in width, but extracted from different planes considering the coordinate system attributed to the foamed block as illustrated in FIG. 8 in which z represents the height of the foamed block and at the same time, the direction at which the cells are preferentially oriented.

Both, EXAMPLES A and B, are sliced from plane xy, although in EXAMPLE A, the length direction of the layer corresponds to the x direction of the foamed block, while in EXAMPLE B the length direction of the layer corresponds to the y direction of the foamed block. In both cases, the cells are oriented parallel to the layer thickness direction. EXAMPLE C is sliced from the two planes (xy and zx) parallel to the height direction of the foamed block (z) in such a way that cells are oriented parallel to the layer length direction (the results obtained for EXAMPLE C will represent the average of the two layers specified here).

The capillarity measurements are carried out by immersing the three EXAMPLES A-C into a recipient filled with synthetic blood (as formulated or prepared by SGS Courtray Laboratories (Oignies, France)) and by measuring the height reached by blood after diffusing against gravity (by holding each sample at 90°—and thus parallel to the direction of gravity) throughout the length direction of the layer for 300 seconds. In EXAMPLES A and B blood encounters cells which are oriented perpendicularly to the direction at which blood diffuses while in EXAMPLE C, blood encountered cells which are oriented parallel to the blood diffusion direction. Measurements are carried out in triplicate for each example.

The degree of orientation of the cells in the layers with respect to the direction at which blood diffuses is quantified by means of measuring the average anisotropy ratio (R) parameter in said direction (using the methods previously described) in three different layers corresponding to each one of the examples mentioned.

Figure 11:
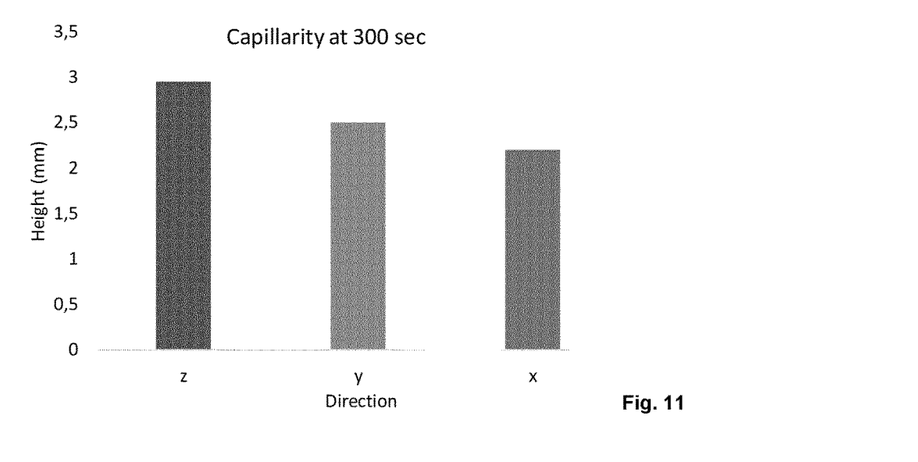
FIG. 11 is a graph showing capillarity of an anisotropic foam according to an aspect of the disclosure in three different directions.

Table 3—shows the results for each of the Examples A to C, and FIG. 11 further shows a graph summarizing the capillarity measurements.

|  | Example A | Example B | Example C |
| --- | --- | --- | --- |
| average anisotropy ratio R | 0.87 ± 0.05 | 1.14 ± 0.12 | 1.78 ± 0.07 |
| average cell size | 209.9 ± 10.7 | 194.2 ± 3.2 | 248.2 ± 20.3 |
| Capillarity (mm) | 2.2 ± 0.15 | 2.5 ± 0.08 | 2.9 ± 0.11 |

Table 3 (and FIG. 11) show improved capillarity along the axis of anisotropy for anisotropic foams.

Stress at 5% strain: The mechanical properties of foams with anisotropic cellular structures are directionally dependent. For this reason, the mechanical properties of the samples described in EXAMPLES A and C are measured under compression (75% of strain; strain rate: 10 s$^{-1}$ using a universal testing machine model 5.500R6025 Instron and employing the following procedure: the layers are placed between the compression plates of the testing machine and are compressed along the thickness direction of the layers in such a way that in EXAMPLE A, cells are oriented parallel to the compression direction and in EXAMPLE C, cells are oriented perpendicular to the compression direction.

Examples A and C are measured both in the dry state and in the wet state (after having absorbed blood) in order to evaluate how they are modified by the fact of absorbing blood.

Table 4—shows the stress results for each of the Examples A and C.

|  | Example A | Example C |
| --- | --- | --- |
| Stress at 5% Strain (kPa) dry | 2.2 ± 0.32 | 1.8 ± 0.12 |
| Stress at 5% Strain (kPa) wet | 1.6 ± 0.11 | 1.6 ± 0.21 |

It is desirable for materials to have at least a stress value greater than that identified and described herein but not too high in order to avoid other disadvantages such as increased overall stiffness of the product. A stress greater than the minimum level identified and described herein but very close thereto may provide a more comfortably perception to the user. It is also interesting to note that the mechanical resistance of the product is reduced when the material is in the wet state improving them the comfortability.

It is supposed that the present invention is not restricted to any form of realization described previously and that some modifications can be added to the presented example of fabrication without reappraisal of the appended claims.

The invention claimed is:

1. An absorbent article (7) comprising a liquid permeable topsheet (8) having a surface, a liquid impermeable backsheet (9), an absorbent core (1) between the topsheet (8) and the backsheet (9) and an acquisition layer (2) between the topsheet (8) and the absorbent core (1), said acquisition layer (2) having an uppermost surface closest to the topsheet (8), a width (w) and a length (l) along an acquisition plane and a thickness (t) extending perpendicular thereto, wherein the absorbent core (1) comprises at least one absorbent material selected from the group consisting of fibrous absorbent materials and highly absorbent polymers, characterized in that the acquisition layer (2) comprises a polymeric foam having an open cell and interconnected porous structure comprising an anisotropic cell structure having an axis of anisotropy (4) extending substantially parallel to a longest length of a plurality of substantially neighbouring cells (6), which is substantially perpendicular to the acquisition plane, and in that the acquisition layer (2) is in direct or indirect contact with the absorbent core (1).

2. An absorbent article according to claim 1, wherein the foam open cells (6) of the acquisition layer have an average anisotropy ratio R of greater than 1.1, as measured according to the method described herein.

3. An absorbent article according to claim 1, wherein the acquisition layer (2) comprises a polymer foam selected from the group consisting of: polyurethane; poly vinyl alcohol (PVA); polyolefins selected from the group consisting of low-density polyethylene (LDPE), ethylene-vinyl acetate (EVA), ethylene butyl acrylate (EBA), and mixtures thereof; open cell silicone foams; natural and synthetic rubbers; and mixtures thereof.

4. An absorbent article according to claim 1, wherein the acquisition layer (2) comprises a polyurethane foam.

5. An absorbent article according to claim 1, wherein the fibrous absorbent materials comprise synthetic fibres, cellulosic fibres, fluff pulp, tissue layers, absorbent nonwoven materials, or any combination of two or more of these absorbent materials and mixture thereof.

6. An absorbent article according to claim 1, wherein the absorbent core (1) comprises cellulosic fluff pulp and superabsorbent polymers.

7. An absorbent article according to claim 1, wherein the absorbent core (1) comprises substantially continuous zones of one or more high fluid distribution structures and discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures.

8. An absorbent article according to claim 1, which further comprises a non-woven layer between the acquisition layer (2) and the absorbent core (1).

9. An absorbent article (7) according to claim 1, wherein the topsheet (8) or the uppermost surface of the acquisition layer (2) closest to said topsheet (8) comprises a coloured area comprising a colour pigment imparting a hue having an ω angle measured in the CIELAB colour scale of from 135° to 315°.

10. An absorbent article (7) according to claim 9, wherein said coloured area extends through the entire surface of the topsheet (8) or the acquisition layer (2); or is located in a central portion of said absorbent article (7) and distal from perimeter edges thereof.

11. An absorbent article (7) according to claim 10, wherein the coloured area is substantially circumscribed by a non-coloured area.

12. An absorbent article (7) according to claim 1, wherein the acquisition layer (2) comprises one or more interconnected macro channels at least on the uppermost surface of the acquisition layer (2), said uppermost surface being opposite the absorbent core (1), and extending at least a portion of the length (l) and width (w) of said acquisition layer (2).

13. An absorbent article (7) according to claim 1, wherein the acquisition layer (2) comprises at least one zone differing in stiffness, said zone comprising at least one aperture.

14. An absorbent article (7) according to claim 1, wherein said absorbent article (7) is selected from the group consisting of sanitary napkins and towels for feminine care, pants and diapers for babies or adult incontinence, and towels or pads for light incontinence.

15. A method of making an absorbent article (7) according to claim 1, the method comprising the steps of:
 (i) providing the acquisition layer (2);
 (ii) laminating said acquisition layer (2) between the liquid permeable topsheet (8) and the absorbent core (1), and further with the liquid impermeable backsheet (9).

16. An absorbent article according to claim 2, wherein the average anisotropy ratio R is from 1.1 to 3.5.

17. An absorbent article according to claim 1, wherein the acquisition layer (2) consists of a polymer foam selected from the group consisting of: polyurethane; poly vinyl alcohol (PVA);
 polyolefins selected from the group consisting of low-density polyethylene (LDPE), ethylene-vinyl acetate (EVA), ethylene butyl acrylate (EBA), and mixtures thereof; open cell silicone foams; natural and synthetic rubbers; and mixtures thereof.

18. An absorbent article according to claim 1, wherein the acquisition layer (2) consists of a polyurethane foam.

19. An absorbent article (7) according to claim 9, wherein said coloured area has an opacity of at least 20%.

20. An absorbent article (7) according to claim 10, wherein said coloured area is positioned such that when said article (7) is worn by a subject the coloured area is proximal to a genital opening through which body fluids are expelled.

21. An absorbent article (7) according to claim 13, wherein the at least one aperture extends across the entire thickness (t) of the acquisition layer.

22. A method of making an absorbent article (7) according to claim 15, wherein the laminating is such that the acquisition layer (2) is in direct or indirect contact with the topsheet (8) and the absorbent core (1), and the absorbent core (1) is in direct or indirect contact with the acquisition layer (2) and the backsheet (9).

* * * * *